US008135476B2

(12) United States Patent
Gerber et al.

(10) Patent No.: US 8,135,476 B2
(45) Date of Patent: Mar. 13, 2012

(54) IMPLANTABLE MEDICAL ELECTRICAL STIMULATION LEAD FIXATION METHOD AND APPARATUS

(75) Inventors: Martin T. Gerber, Maple Grove, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/380,499

(22) Filed: Apr. 27, 2006

(65) Prior Publication Data
US 2007/0255366 A1 Nov. 1, 2007

(51) Int. Cl.
*A61N 1/05* (2006.01)

(52) U.S. Cl. ........ 607/116; 607/117; 607/126; 607/127; 607/128; 607/129; 607/122; 607/119

(58) Field of Classification Search ........... 607/116, 607/117, 126–129, 119, 122
See application file for complete search history.

(56) References Cited

U.S. PATENT DOCUMENTS

| | | | |
|---|---|---|---|
| 4,414,986 A * | 11/1983 | Dickhudt et al. | ............. 607/117 |
| 4,419,819 A | 12/1983 | Dickhudt et al. | |
| 4,465,079 A | 8/1984 | Dickhudt | |
| 4,519,403 A | 5/1985 | Dickhudt | |
| 5,003,992 A | 4/1991 | Holleman et al. | |
| 5,090,422 A | 2/1992 | Dahl et al. | |
| 5,129,404 A | 7/1992 | Spehr et al. | |
| 5,207,672 A | 5/1993 | Roth et al. | |
| 5,215,105 A | 6/1993 | Kizelshteyn | |
| 5,387,233 A | 2/1995 | Alferness et al. | |
| 5,456,667 A | 10/1995 | Ham et al. | |
| 5,484,445 A | 1/1996 | Knuth | |
| 5,531,779 A | 7/1996 | Dahl et al. | |
| 5,545,193 A | 8/1996 | Fleischman et al. | |
| 5,723,718 A | 3/1998 | Berens | |
| 5,865,843 A | 2/1999 | Baudino | |
| 5,957,965 A | 9/1999 | Moumane et al. | |
| 5,957,966 A * | 9/1999 | Schroeppel et al. | .......... 607/122 |
| 6,055,457 A | 4/2000 | Bonner | |
| 6,077,298 A | 6/2000 | Tu et al. | |
| 6,104,960 A | 8/2000 | Duysens et al. | |
| 6,161,029 A | 12/2000 | Spreigl et al. | |
| 6,322,559 B1 | 11/2001 | Daulton et al. | |

(Continued)

FOREIGN PATENT DOCUMENTS

CA 2527976 A1 7/2006

(Continued)

OTHER PUBLICATIONS

Lendlein, et al., "Biodegradable, Elastic Shape-Memory Polymers for Potential Biomedical Applications", Science, May 2002, 296:5573, p. 1673-1676.

(Continued)

*Primary Examiner* — Niketa Patel
*Assistant Examiner* — Joseph Stoklosa

(57) ABSTRACT

An implantable medical electrical lead for electrical stimulation of body tissue that includes at least one shape memory polymer portion that has a first configuration and a second configuration, wherein the second configuration is obtained upon exposure of the shape memory polymer portion to a transition stimulus, and wherein the second configuration of the modifiable portion exhibits a greater resistance to movement of the lead within the body tissue than does the first configuration; and at least one electrode configured to provide electrical stimulation of body tissue, wherein the lead has a proximal end and a distal end. Systems and kits as well as methods of utilizing the leads of the invention are also included.

23 Claims, 11 Drawing Sheets

U.S. PATENT DOCUMENTS

| | | | | |
|---|---|---|---|---|
| 6,325,797 | B1* | 12/2001 | Stewart et al. | 606/41 |
| 6,388,043 | B1 | 5/2002 | Langer et al. | |
| 6,510,347 | B2 | 1/2003 | Borkan | |
| 6,580,949 | B1 | 6/2003 | Tsuboi et al. | |
| 6,704,604 | B2 | 3/2004 | Soukup et al. | |
| 6,711,443 | B2 | 3/2004 | Osypka | |
| 6,720,402 | B2 | 4/2004 | Langer et al. | |
| 6,814,733 | B2 | 11/2004 | Schwartz et al. | |
| 6,909,920 | B2 | 6/2005 | Thompson | |
| 6,952,613 | B2 | 10/2005 | Swoyer et al. | |
| 6,999,819 | B2 | 2/2006 | Swoyer et al. | |
| 7,099,718 | B1 | 8/2006 | Thacker et al. | |
| 7,107,105 | B2 | 9/2006 | Bjorklund et al. | |
| 7,155,293 | B2 | 12/2006 | Westlund et al. | |
| 7,272,448 | B1* | 9/2007 | Morgan et al. | 607/129 |
| 2002/0077684 | A1 | 6/2002 | Clemens et al. | |
| 2002/0095114 | A1 | 7/2002 | Palasis | |
| 2002/0147485 | A1 | 10/2002 | Mamo et al. | |
| 2003/0050681 | A1 | 3/2003 | Pianca et al. | |
| 2003/0199961 | A1 | 10/2003 | Bjorklund et al. | |
| 2004/0176782 | A1 | 9/2004 | Hanse et al. | |
| 2004/0215237 | A1 | 10/2004 | Christopherson et al. | |
| 2004/0230279 | A1 | 11/2004 | Cates et al. | |
| 2004/0230280 | A1 | 11/2004 | Cates et al. | |
| 2004/0230281 | A1 | 11/2004 | Heil et al. | |
| 2005/0038491 | A1 | 2/2005 | Haack | |
| 2005/0060014 | A1 | 3/2005 | Swoyer et al. | |
| 2005/0096718 | A1 | 5/2005 | Gerber et al. | |
| 2005/0288781 | A1 | 12/2005 | Moaddeb et al. | |
| 2006/0041089 | A1 | 2/2006 | Mather et al. | |
| 2006/0079949 | A1 | 4/2006 | Hine et al. | |
| 2006/0247753 | A1 | 11/2006 | Wenger et al. | |
| 2007/0073130 | A1* | 3/2007 | Finch et al. | 600/372 |
| 2007/0255365 | A1 | 11/2007 | Gerber | |
| 2007/0255383 | A1 | 11/2007 | Gerber | |
| 2007/0261115 | A1 | 11/2007 | Gerber | |

FOREIGN PATENT DOCUMENTS

| | | |
|---|---|---|
| EP | 861676 | 2/1998 |
| WO | WO-02087690 | 11/2002 |
| WO | WO-2004047914 | 6/2004 |

OTHER PUBLICATIONS

Lendlein, "Shape Memory Polymers—Biodegradable Sutures", Abstracted from Materials World, Jul. 2002, 10:7, p. 29-30, Website Article: www.azom.com/details.asp?articleID=1542.

Wingfield, "Shape Change Materials", Feb. 2006: 13:08, Website Article: www.loop.ph/twiki/bin/view/Openloop/ShapeChange.

Gerber, Implantable Medical Electrical Stimulation Lead Fixation Method and Apparatus, U.S. Appl. No. 11/380,480, Final Office Action May 13, 2009.

Gerber, Implantable Medical Electrical Stimulation Lead Fixation Method and Apparatus, U.S. Appl. No. 11/380,480, Non-Final Office Action Nov. 28, 2008.

Gerber, Implantable Medical Electrical Stimulation Lead Fixation Method and Apparatus, U.S. Appl. No. 11/380,480, Advisory Action Sep. 9, 2008.

Gerber, Implantable Medical Electrical Stimulation Lead Fixation Method and Apparatus, U.S. Appl. No. 11/380,480, Final Office Action Apr. 30, 2008.

Gerber, Implantable Medical Electrical Stimulation Lead Fixation Method and Apparatus, U.S. Appl. No. 11/380,480, Non-Final Office Action Aug. 22, 2007.

Gerber, Implantable Medical Electrical Stimulation Lead Fixation Method and Apparatus, U.S. Appl. No. 11/380,493, Final Office Action Aug. 25, 2009.

Gerber, Implantable Medical Electrical Stimulation Lead Fixation Method and Apparatus, U.S. Appl. No. 11/380,493, Non-Final Office Action Feb. 27, 2009.

Gerber, Implantable Medical Electrical Stimulation Lead Fixation Method and Apparatus, U.S. Appl. No. 11/380,493, Final Office Action Oct. 6, 2008.

Gerber, Implantable Medical Electrical Stimulation Lead Fixation Method and Apparatus, U.S. Appl. No. 11/380,493, Non-Final Office Action Feb. 12, 2008.

Gerber et al., Implantable Medical Electrical Stimulation Lead Fixation Method and Apparatus, U.S. Appl. No. 11/380,511, Non-Final Office Action Mar. 5, 2009.

Gerber et al., Implantable Medical Electrical Stimulation Lead Fixation Method and Apparatus, U.S. Appl. No. 11/380,511, Advisory Action Oct. 30, 2008.

Gerber et al., Implantable Medical Electrical Stimulation Lead Fixation Method and Apparatus, U.S. Appl. No. 11/380,511, Final Office Action Jul. 28, 2008.

Gerber et al., Implantable Medical Electrical Stimulation Lead Fixation Method and Apparatus, U.S. Appl. No. 11/380,511, Non-Final Office Action Nov. 15, 2007.

U.S. Appl. No. 11/380,493, Office Action dated Dec. 7, 2009.

U.S. Appl. No. 10/380,480 Non-Final Office Action dated Oct. 26, 2009.

U.S. Appl. No. 10/380,511 Non-Final Office Action dated Oct. 30, 2009.

U.S. Appl. No. 11/380,480 response filed Jan. 26, 2010.

U.S. Appl. No. 11/380,480 Office Action dated Apr. 30, 2010.

U.S. Appl. No. 11/380,480 response filed Jun. 16, 2010.

U.S. Appl. No. 11/380,493 Office Action dated Dec. 7, 2009.

U.S. Appl. No. 11/380,493 response filed Mar. 5, 2010.

U.S. Appl. No. 11/380,511 response filed Feb. 1, 2010.

U.S. Appl. No. 11/380,511 Office Action dated May 3, 2010.

U.S. Appl. No. 11/380,480 response filed Feb. 18, 2008.

U.S. Appl. No. 11/380,480 response filed Jun. 25, 2008.

U.S. Appl. No. 11/380,480 response filed Mar. 2, 2009.

U.S. Appl. No. 11/380,480 response filed Aug. 13, 2009.

U.S. Appl. No. 11/380,493 response May 12, 2008.

U.S. Appl. No. 11/380,493 supplemental response Sep. 22, 2008.

U.S. Appl. No. 11/380,493 response Jan. 6, 2009.

U.S. Appl. No. 11/380,493 response May 22, 2009.

U.S. Appl. No. 11/380,493 response Nov. 25, 2009.

U.S. Appl. No. 11/380,511 response filed Apr. 15, 2008.

U.S. Appl. No. 11/380,511 response filed Sep. 28, 2008.

U.S. Appl. No. 11/380,511 response filed Dec. 30, 2008.

U.S. Appl. No. 11/380,511 response filed Jul. 4, 2009.

U.S. Appl. No. 11/380,493 Final Office Action dated Jun. 25, 2010.

U.S. Appl. No. 11/380,493 response filed Aug. 25, 2010.

U.S. Appl. No. 11/380,480 Advisory Action dated Jul. 8, 2010.

U.S. Appl. No. 11/380,480 Response filed Aug. 25, 2010.

U.S. Appl. No. 11/380,480 Non-Final Office Action dated Oct. 4, 2010.

U.S. Appl. No. 11/380,493 Advisory Action dated Oct. 1, 2010.

U.S. Appl. No. 11/380,511 response filed Aug. 2, 2010.

U.S. Appl. No. 11/380,480 response filed Dec. 29, 2010.

U.S. Appl. No. 11/380,493 response filed Nov. 24, 2010.

U.S. Appl. No. 11/380,511 Final Office Action dated Nov. 12, 2010.

U.S. Appl. No. 11/380,511 response filed Feb. 14, 2011.

U.S. Appl. No. 11/380,480 Final Office Action mailed Mar. 4, 2011.

U.S. Appl. No. 11/380,480 Response filed Jun. 6, 2011.

U.S. Appl. No. 11/380,480 Non-Final Office Action mailed Jun. 23, 2011.

U.S. Appl. No. 11/380,480 Response filed Sep. 23, 2011.

* cited by examiner

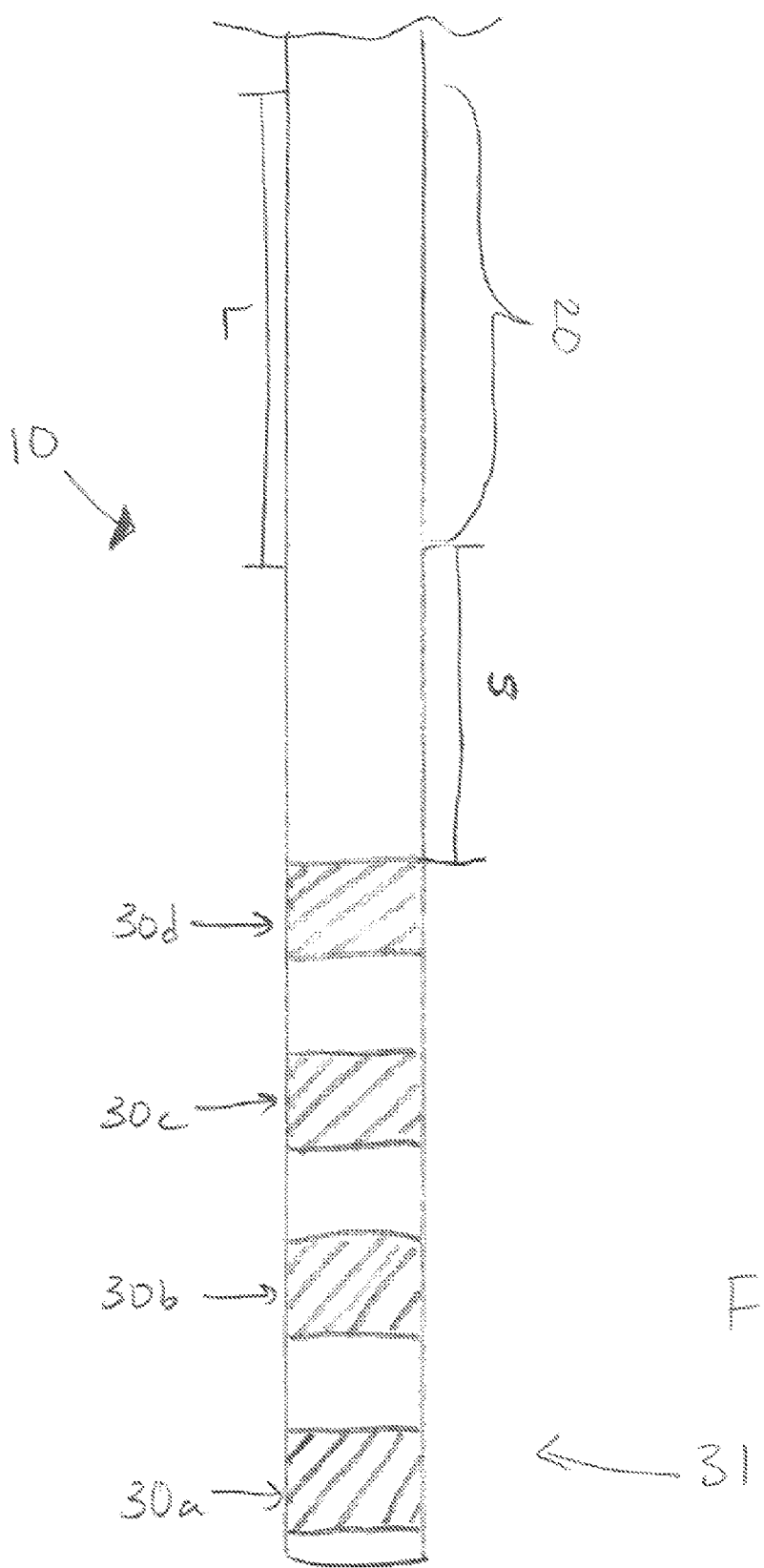

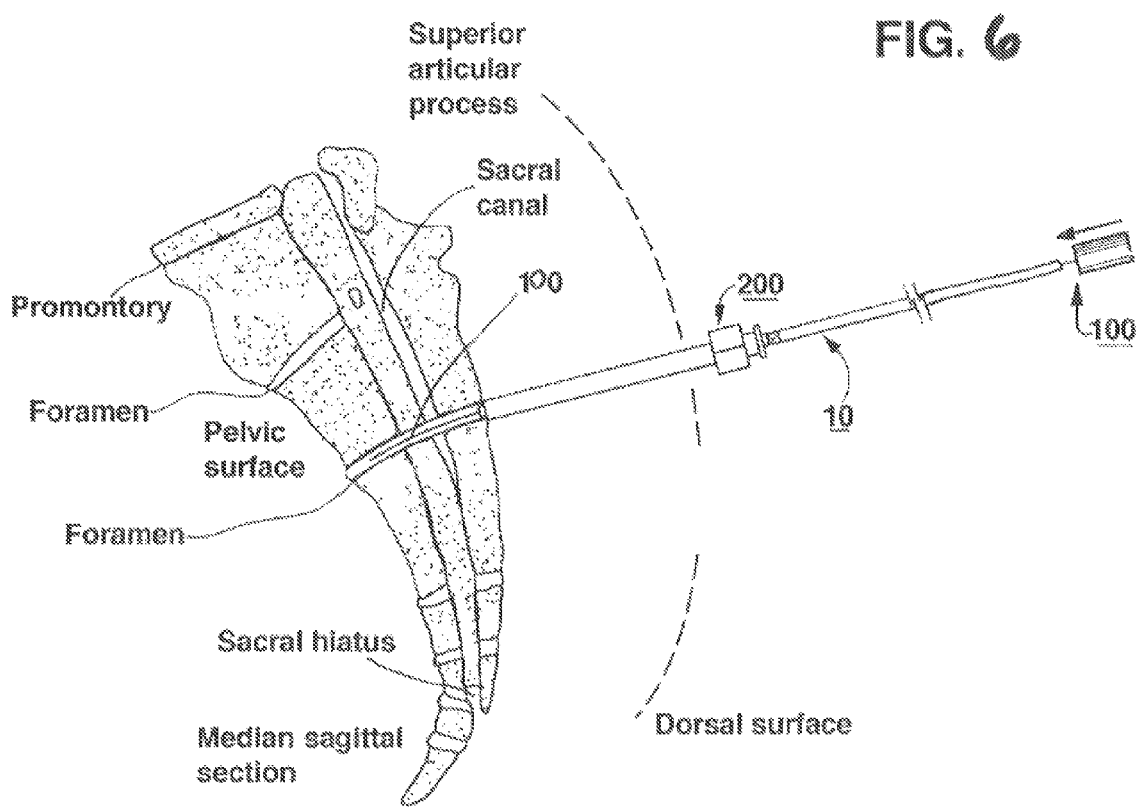

IMPLANTABLE MEDICAL ELECTRICAL STIMULATION LEAD FIXATION METHOD AND APPARATUS

FIELD OF THE INVENTION

This invention relates generally to device for electrical stimulation of body tissue. More specifically, this invention relates to an implantable medical electrical lead having at least one stimulation electrode and a fixation mechanism for fixing the lead within the tissue.

BACKGROUND OF THE INVENTION

Pelvic floor disorders such as, urinary incontinence, urinary urge/frequency, urinary retention, pelvic pain, bowel dysfunction (constipation, diarrhea), and erectile dysfunction, involve bodily functions that are influenced by the sacral nerves. Specifically, urinary incontinence is the involuntary control over the bladder that is exhibited in various patients. Urinary incontinence is primarily treated through pharmaceuticals and surgery. Many of the pharmaceuticals do not adequately resolve the issue and can cause unwanted side effects, and a number of the surgical procedures have a low success rate and are not reversible. Several other methods have been used to control urinary incontinence, for example, vesicostomy or an artificial sphincter implanted around the urethra. These solutions have drawbacks well known to those skilled in the art. In addition, the other mentioned disorders do not have adequate pharmaceutical or surgical treatment options.

The organs involved in bladder, bowel, and sexual function receive much of their control via the sacral nerves, in some instances the second, third, and fourth sacral nerves, commonly referred to as S2, S3 and S4 respectively. Electrical stimulation of these various nerves has been found to offer some control over these functions.

Neurostimulation leads with at least one stimulation electrode positioned on or near the sacral nerves of the human body have been implanted to provide partial control for urinary incontinence. Temporary sacral nerve stimulation is accomplished through implantation of a temporary neurostimulation lead extending through the skin and connected with a temporary external pulse generator as described for example in commonly assigned U.S. Pat. Nos. 5,957,965 and 6,104,960. A permanent neurostimulator can be implanted if the temporary stimulation is efficacious and it is possible to do so in the particular patient. Permanent implantation can be accomplished by implanting a permanent neurostimulation lead, extending the proximal portion of the lead body subcutaneously, and connecting its proximal end with an implantable pulse generator (IPG) implanted subcutaneously.

One problem that can be associated with implantation of both permanent and temporary neurostimulation leads involves maintaining the electrode(s) in casual contact, that is in a location where slight contact of the electrode with the sacral nerve may occur or in close proximity to the sacral nerve to provide adequate stimulation of the sacral nerve, while allowing for some axial movement of the lead body. In order to minimize the movement of the lead, the lead body is fixed to retard migration and dislodgement of the electrodes from the optimal position. This can be accomplished by employing sutures or a sacral lead fixation mechanism, an example of which is described in commonly assigned U.S. Pat. No. 5,484,445. An example of a lead that includes a fixation mechanism can be found in commonly assigned U.S. Pat. No. 6,999,819, the disclosure of which is incorporated herein by reference. Although the fixation mechanisms of the above referenced patents are a significant advance over the prior art, there are still further advantages to be gained. For example, it can be difficult to place those leads because once the tines are released from the dilator sheath, the tines deploy and it becomes impossible to retract the lead body and position it again. Therefore, there remains a need for a lead having a fixation mechanism that can be easily repositioned.

SUMMARY OF THE INVENTION

The invention includes an implantable medical electrical lead for electrical stimulation of body tissue that includes at least one shape memory polymer portion that has a first configuration and a second configuration, wherein the second configuration is obtained upon exposure of the shape memory polymer portion to a transition stimulus, and wherein the second configuration of the modifiable portion exhibits a greater resistance to movement of the lead within the body tissue than does the first configuration, and at least one electrode configured to provide electrical stimulation of body tissue, wherein the lead has a proximal end and a distal end The invention also includes a kit that includes an implantable medical electrical lead for electrical stimulation of body tissue that includes at least one electrode, a lead body, at least one shape memory polymer portion that has a first configuration and a second configuration, wherein the second configuration is obtained upon exposure of the shape memory polymer portion to a transition stimulus, and wherein the second configuration of the modifiable portion exhibits a greater resistance to movement of the lead within the body tissue than does the first configuration; and a source of a transition stimulus The invention further includes a medical electrical stimulation system that includes an implantable pulse generator for providing medical electrical stimulation; and an implantable medical electrical lead for electrical stimulation of body tissue that includes at least one shape memory polymer portion that has a first configuration and a second configuration, wherein the second configuration is obtained upon exposure of the shape memory polymer portion to a transition stimulus, and wherein the second configuration of the modifiable portion exhibits a greater resistance to movement of the lead within the body tissue than does the first configuration; and at least one electrode configured to provide electrical stimulation of body tissue.

The invention also includes a method of providing electrical stimulation of body tissue at a stimulation site employing an implantable pulse generator that includes providing an implantable medical lead that includes at least one shape memory polymer portion that has a first configuration and a second configuration, wherein the second configuration is obtained upon exposure of the shape memory polymer portion to a transition stimulus, and wherein the second configuration of the modifiable portion exhibits a greater resistance to movement of the lead within the body tissue than does the first configuration, at least one electrode configured to provide electrical stimulation of body tissue, and at least one proximal connector element formed in a connector array in a proximal segment of the lead body; percutaneously introducing the implantable medical lead adjacent to the stimulation site; applying a transition stimulus to at least the at least one shape memory polymer portion of the lead; and coupling the at least one proximal connector element with the implantable pulse generator.

The full range of advantages and features of this invention are only appreciated by a full reading of this specification and a full understanding of the invention. Therefore, to complete this specification, a detailed description of the invention and the preferred embodiments follow, after a brief description of the drawings, wherein additional advantages and features of the invention are disclosed.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Embodiments of the invention are illustrated in the drawings, wherein like reference numerals refer to like elements in the various views. Furthermore, it will be understood by one of skill in the art that the drawings are not drawn to scale.

FIG. 5 is a diagram illustrating a portion of a lead in accordance with the invention.

FIG. 6 is a cross-section view of the sacrum schematically illustrating an initial step of implanting a lead of the invention before the shape memory polymer portion of the lead is exposed to a transition stimulus.

DETAILED DESCRIPTION OF THE INVENTION

A lead in accordance with the invention can be utilized to provide neurostimulation or neuromodulation to any portion of the nervous system within the body of a patient. In one embodiment a lead in accordance with the invention can be utilized in any target tissue that requires some amount of fixation or traction to minimize movement of the lead. In one embodiment the lead can be implanted within muscle or connective tissue to stimulate or modulate peripheral nerves within that tissue.

A lead in accordance with the invention can be placed anywhere within the body where electrical stimulation is desired. In one embodiment a lead in accordance with the invention can be utilized to provide neurostimulation within the pelvic region of a patient. In such an embodiment the lead may be positioned to provide stimulation to one or more of the sacral nerves. Sacral nerves that may be stimulated using a lead in accordance with the invention include, but are not limited to the pudendal nerve, the pelvic splanchnic nerve, the cavernosa nerve in the penis or nerves located in or near the clitoris in a female, the hypogastric nerve, the vesicle nerve plexus, the perineal nerves, the pelvic nerve plexus, the prostate gland, the prostatic plexus nerve, the vagina, the anus, the urethra, the penis dorsal nerve, the inferior rectal nerves, the scrotal nerves, scrotum, Alcock's Canal, the sacro-tuberous ligament, the ischial tuberosity, the greater sciatic foramen, the lesser sciatic foramen, and other nerves or nerve portions located in the general region of the pelvic floor.

Neurostimulation using a lead in accordance with the invention can be utilized to treat any of a number of conditions including, but not limited to pelvic floor disorders such as urinary control disorders, fecal control disorders, sexual dysfunction, pelvic pain, interstitial cystitis, endometriosis, and genital pain such as vulvodynia or idiopathic chronic testicular pain. Although the invention is discussed with respect to stimulation of one or more nerves within the pelvic floor for the treatment of urinary incontinence, it will be understood by one of skill in the art, that leads of the invention can be utilized to treat other disorders or conditions by stimulating other nerves.

In one embodiment, a lead in accordance with the invention can be used with a therapy for treating urinary incontinence, such as MEDTRONIC INTERSTIM® Therapy. For example, an implantable neurostimulation system may stimulate organs involved in urinary, fecal or sexual function via C-fibers or sacral nerves at the second, third, and fourth sacral nerve positions, commonly referred to as S2, S3, and S4, respectively. In another embodiment a lead in accordance with the invention can be used with a therapy for treating gastroparesis, such as MEDTRONIC ENTERRA® Therapy.

Figure 1A:
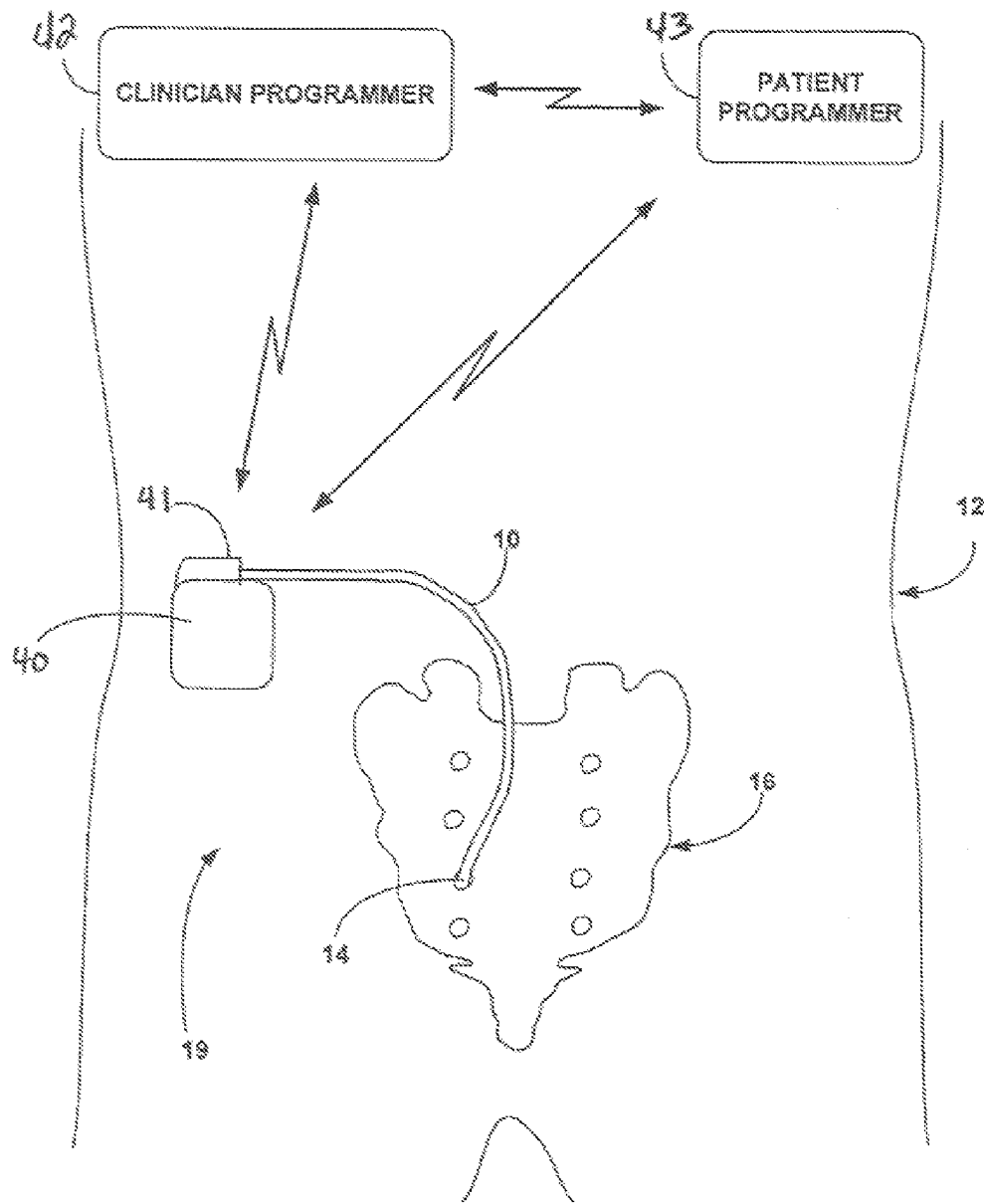
FIG. 1A is a diagram illustrating an implantable neurostimulator system for stimulating nerves, such as sacral nerves via a lead.

FIG. 1A is a diagram illustrating an implantable neurostimulation system 19 for stimulating a nerve, such as a sacral nerve, via lead 10. Lead 10 is generically depicted in FIG. 1A, and does not necessarily depict all of the features of a lead in accordance with the invention. Neurostimulation system 19 delivers neurostimulation to the sacral nerves or other regions of the nervous system known to treat pelvic floor disorders, urinary control disorders, fecal control disorders, interstitial cystitis, sexual dysfunction, and pelvic pain. Again, neurostimulation system 19 and lead 10 may be useful in other neurostimulation applications, such as spinal cord stimulation, deep brain stimulation, gastric stimulation, and the like. As shown in FIG. 1A, system 19 includes lead 10 and an implantable neurostimulator 40. In addition, a proximal end 32 of stimulation lead 10 may be coupled to a connector block 41 associated with neurostimulator 40.

Neurostimulator 40 includes an implantable pulse generator, and delivers neurostimulation therapy to patient 12 in the form of electrical pulses generated by the implantable pulse generator. In the example of FIG. 1A, neurostimulator 40 is implanted in the upper left buttock of patient 12, but may be implanted at other locations. An example of a commercially available neurostimulator includes, but is not limited to MEDTRONIC® Model 3023 Neurostimulator.

Lead 10 carries one or more stimulation electrodes, for example, 1 to 8 electrodes, to permit delivery of electrical stimulation to sacral nerves. Embodiments of the invention may have 1, 2, 3, 4, 5, 6, 7, 8 or more electrodes. The at least one electrode 30 can include ring electrodes, coil electrodes, circumferential segment electrodes, or any combination thereof. One embodiment of a lead in accordance with the invention has at least two (2) electrodes. Another embodiment of a lead in accordance with the invention has at least four (4) electrodes. In one embodiment having at least four electrodes, at least one of those electrodes can be a coil electrode. In another embodiment of the invention having at least four electrodes, at least one electrode is a coil electrode and at least one of the other electrodes is a ring electrode.

The at least one electrode 30 can be made of any commonly utilized material as is known to those of skill in the art. In one embodiment the at least one electrode 30 is made of a solid surface, bio-compatible material, examples of such materials include, but are not limited to, platinum, a platinum-iridium alloy, or stainless steel for example. Also, in some embodiments, lead 10 may carry one or more electrodes capable of sensing one or more parameters to permit neurostimulator 40 to sense electrical signals within sacrum 16, for example. In some embodiments, neurostimulator 40 may be coupled to two or more leads deployed at different positions, for example, relative to the spinal cord or sacral nerves.

In one embodiment lead 10 includes an outer lead body defining an inner lumen that contains one or more conductors to electrically couple the one or more electrodes to terminals within neurostimulator 40. In one embodiment the lead body outer diameter can be from about 0.5 mm to about 2 mm. In yet another embodiment, the lead body outer diameter is about 1 mm to about 1.5 mm. In a further embodiment the lead body outer diameter is about 1.3 mm.

Leads in accordance with the invention can have variable lengths, depending at least in part on considerations such as the type of tissue that the lead is to be implanted in, the surrounding anatomy where the lead will be implanted, the particular configuration of the lead, the number of modifiable portions within the lead, the number of electrodes within the lead, the location of the one or more modifiable portions and/or the one or more electrodes within the lead, whether or not the lead will be used with an extension, and where the neurostimulator is to be implanted, for example.

In one embodiment of the invention, where the lead is to be used for stimulation of the pelvic floor with a lead extension, the length of the lead can range from about 10 cm to about 100 cm. In another embodiment of the invention, where the lead is to be used for stimulation of the pelvic floor with a lead extension, the length of the lead can range from about 10 cm to about 80 cm. In yet another embodiment of the invention, where the lead is to be used for stimulation of the pelvic floor with a lead extension, the length of the lead can range from about 20 cm to about 60 cm.

Figure 1B:
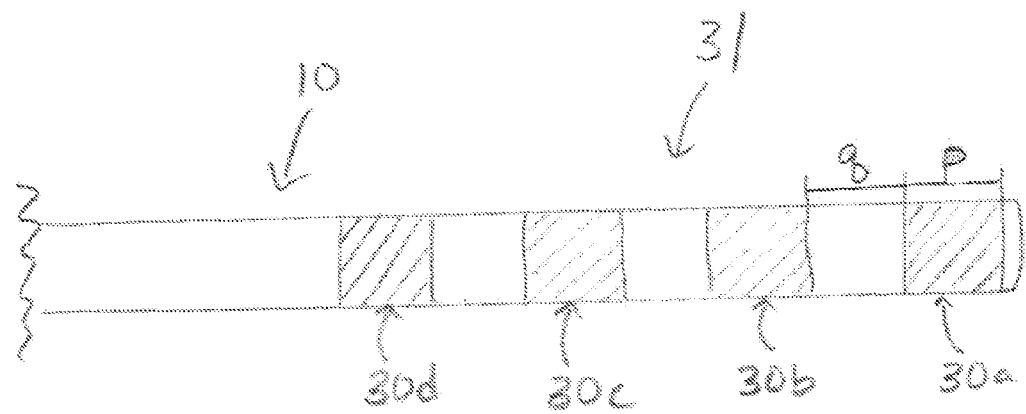
FIG. 1B is a diagram illustrating a portion of a lead in accordance with the invention.

In one embodiment, the at least one electrode 30 is located towards the distal end 31 of the lead 10. FIG. 1B depicts a portion of an exemplary lead 10 in accordance with the invention. The exemplary lead 10 depicted there includes four electrodes 30a, 30b, 30c, and 30d. The electrodes 30a, 30b, 30c, and 30d have an electrode length p. In this example, the four electrodes 30a, 30b, 30c, and 30d have equal electrode lengths p. One of skill in the art, having read this specification, will understand that the electrode lengths p could be different or the same. One of skill in the art will also understand that the electrode lengths p of any one electrode or all of the electrodes can vary and may be at least in part dependent on a number of factors including, but not limited to the type of tissue that the lead will be implanted in, the surrounding anatomy where the lead will be implanted, the stimulation parameters that the lead will be delivering, the types of electrodes, and the number of electrodes.

In one embodiment, the electrode length p can range from about 1 mm to about 20 mm. In another embodiment the electrode length p can range from about 1 mm to about 3 mm. In yet another embodiment the electrode length p can range from about 3 mm to about 10 mm. In one embodiment, a lead 10 has at least one electrode that has an electrode length p of about 3 mm. In another embodiment, a lead 10 has at least one electrode that has an electrode length p of about 10 mm.

The electrodes 30a, 30b, 30c, and 30d are separated by inter-electrode distances q. In this example, the four electrodes 30a, 30b, 30c, and 30d are separated by equal inter-electrode distances q, but one of skill in the art, having read this specification, will understand that the inter-electrode distances q could be different. One of skill in the art, having read this specification, will also understand that the inter-electrode distances q of any one electrode or all of the electrodes can vary and may be at least in part dependent on a number of factors including, but not limited to the type of tissue that the lead will be implanted in, the surrounding anatomy where the lead will be implanted, the stimulation parameters that the lead will be delivering, the types of electrodes, and the number of electrodes.

In one embodiment, the inter-electrode distances q can range from about 0.5 mm to about 5 mm. In another embodiment the inter-electrode distances q can range from about 1 mm to about 2 mm. In yet another embodiment the inter-electrode distances q can range from about 1.2 mm to about 1.6 mm. In one embodiment, a lead 10 has at least two electrodes that have an inter-electrode distance q of about 1.5 mm. In another embodiment, a lead 10 has at least two electrodes that have an inter-electrode distance q of about 3 mm.

Figure 1C:
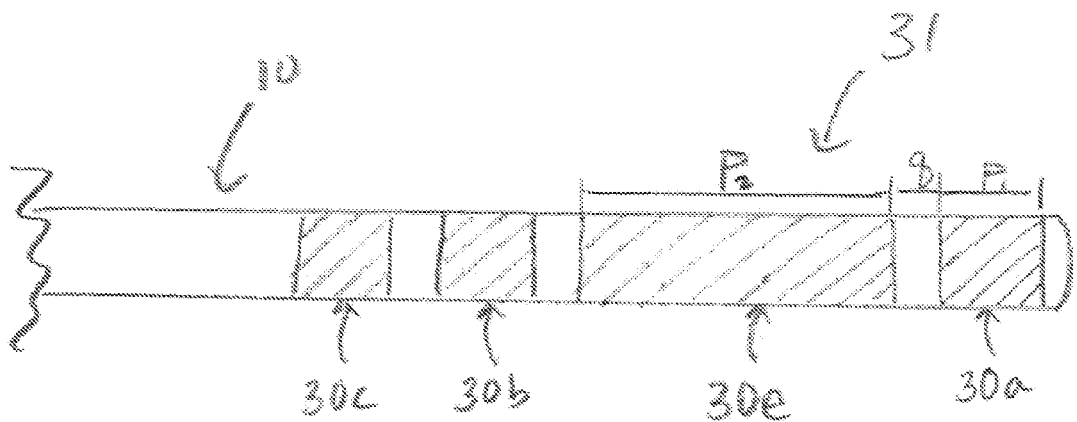
FIG. 1C is a diagram illustrating a portion of a lead in accordance with the invention.

The exemplary lead depicted in FIG. 1C also includes four electrodes 30a, 30b, 30c, and 30e in which only three of the electrodes 30a, 30b, and 30c have the same electrode lengths $p_1$, and the fourth electrode 30e has a different electrode length $p_2$. One of skill in the art, having read this specification, will understand that any combination of equal and unequal electrode lengths $p_1$-$p_2$ are included within the scope of this invention. In one embodiment of the invention, a lead includes four ring electrodes with the same electrode lengths p. In another embodiment of the invention, a lead includes three ring electrodes with the same electrode lengths p and one coil electrode with a different electrode length p.

The at least one electrode can be electrically coupled to the distal end of a coiled wire lead conductor within the body of the lead. The proximal ends of the separately insulated lead conductors can each be coupled to respective connector elements, for example ring-shaped connector elements, in a proximal connector element array in the body of the lead. In one embodiment, the conductor wires can be formed of an MP35N alloy and are insulated from one another within an insulating polymer sheath such as polyurethane, fluoropolymer or silicone rubber for example. The lead conductor wires can be separately insulated by an insulation coating and can be wound in a quadra-filar manner having a common winding diameter within the outer sheath. The coil formed by the coiled wire conductors defines a lead body lumen of the lead body. It will be understood that a further inner tubular sheath could be interposed within the aligned wire coils to provide the lead body lumen.

The connector elements can be adapted to be coupled with a neurostimulator IPG, additional intermediate wiring, or other stimulation device adapted to be implanted subcutaneously. An example of such an implantable pulse generator is the MEDTRONIC® Neurostimulator Model 3023. Electrical stimulation pulses generated by the neurostimulator IPG are applied to a nerve or nerves, such as the sacral nerve, through the at least one electrode in either a unipolar or bipolar stimulation mode.

As further shown in FIG. 1A, implantable neurostimulation system 19 also may include a clinician programmer 42 and a patient programmer 43. Clinician programmer 42 may be a handheld computing device that permits a clinician to program neurostimulation therapy for patient 12, e.g., using input keys and a display. For example, using clinician programmer 42, the clinician may specify neurostimulation parameters for use in delivery of neurostimulation therapy.

Clinician programmer 42 supports radio frequency telemetry with neurostimulator 40 to download neurostimulation parameters and, optionally, upload operational or physiological data stored by neurostimulator. In this manner, the clinician may periodically interrogate neurostimulator 40 to evaluate efficacy and, if necessary, modify the stimulation parameters.

Like clinician programmer 42, patient programmer 43 may be a handheld computing device. Patient programmer 43 may also include a display and input keys to allow patient 12 to interact with patient programmer 43 and implantable neurostimulator 40. In this manner, patient programmer 43 provides patient 12 with an interface for control of neurostimulation therapy by neurostimulator 40.

For example, patient 12 may use patient programmer 43 to start, stop or adjust neurostimulation therapy. In particular, patient programmer 43 may permit patient 12 to adjust stimulation parameters such as duration, amplitude, pulse width and pulse rate, within an adjustment range specified by the clinician via clinician programmer 42.

Neurostimulator 40, clinician programmer 42 and patient programmer 43 may communicate via wireless communication, as shown in FIG. 1A. Clinician programmer 42 and patient programmer 43 may, for example, communicate via wireless communication with neurostimulator 40 using RF telemetry techniques known in the art. Clinician programmer 42 and patient programmer 43 also may communicate with each other using any of a variety of local wireless communication techniques, such as RF communication according to the 802.11 or Bluetooth specification sets, or other standard or proprietary telemetry protocols.

Figure 1D:
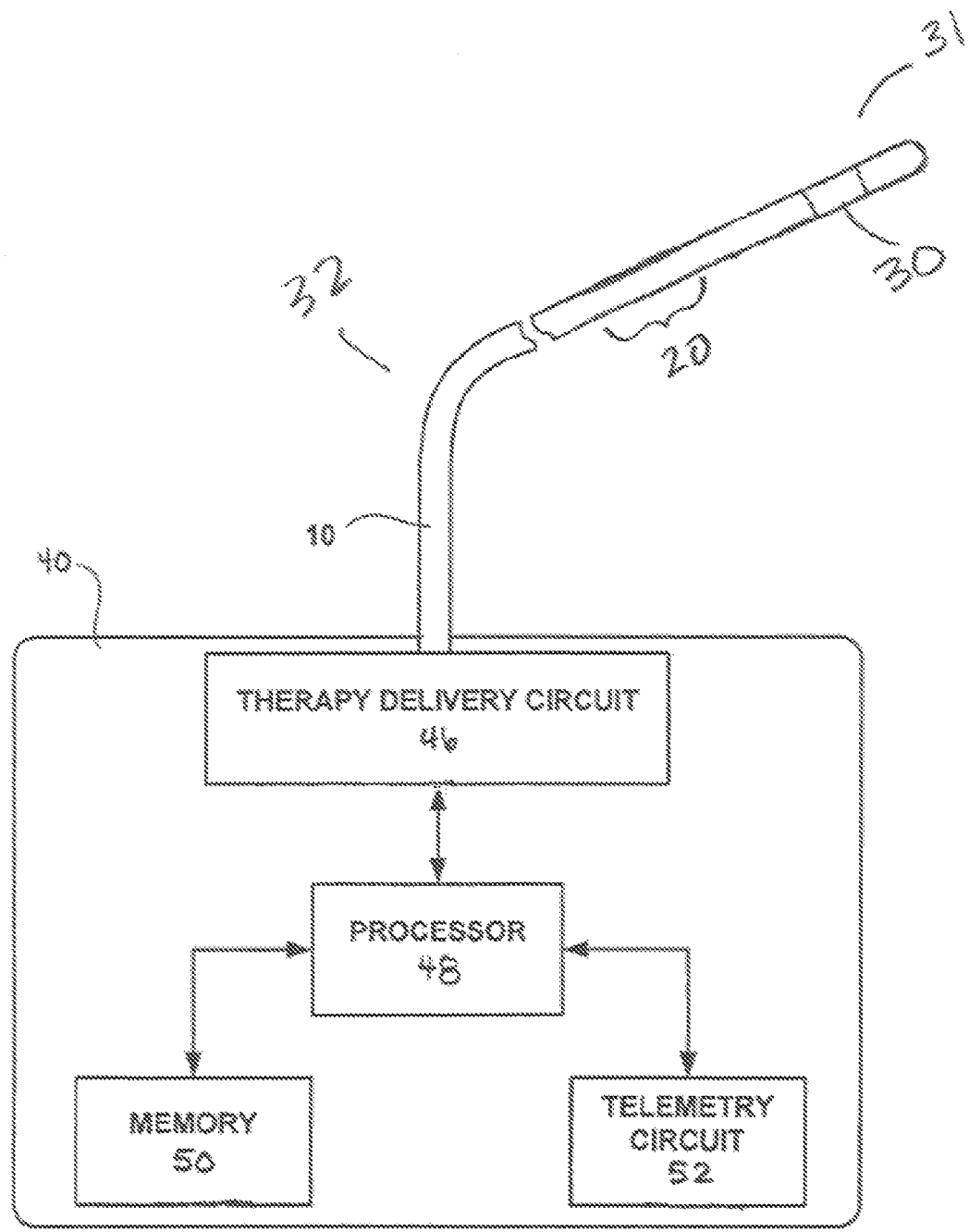
FIG. 1D is a block diagram illustrating various components of an implantable neurostimulator with an implantable lead incorporating a fixation mechanism.

FIG. 1D is a block diagram illustrating various components of an implantable neurostimulator 40 incorporating an implantable lead 10 with a modifiable portion 20. As shown in FIG. 1D, neurostimulator 40 delivers neurostimulation therapy via at least one electrode 30 of lead 10. Electrode 30 is electrically coupled to a therapy delivery circuit 46 via conductors within lead 10. Therapy delivery circuit 46 may, for example, include an implantable pulse generator coupled to a power source such as a battery. The implantable pulse generator within therapy delivery circuit 46 delivers electrical pulses to patient 12 via the at least one electrode 30 under the control of a processor 48.

Processor 48 controls the implantable pulse generator within therapy delivery circuit 46 to deliver neurostimulation therapy according to selected stimulation parameters. In one embodiment, processor 48 can control therapy delivery circuit 46 to deliver electrical pulses with selected amplitudes, pulse widths, rates, or some combination thereof as specified by the program(s). In addition, processor 48 can also control therapy delivery circuit 46 to deliver the neurostimulation pulses via selected subsets of one or more electrodes 30 with selected polarities.

Processor 48 may control therapy delivery circuit 46 to deliver each pulse according to a different program, thereby interleaving programs to simultaneously treat different symptoms or provide a combined therapeutic effect. For example, in addition to treatment of one symptom such as sexual dysfunction, neurostimulator 40 may be configured to deliver neurostimulation therapy to treat other symptoms such as pain or incontinence. Processor 48 may include a microprocessor, a controller, a digital signal processor (DSP), an application-specific integrated chip (ASIC), a field-programmable gate array (FPGA), discrete logic circuitry, or the like.

Neurostimulator 40 also includes a memory 50. In some embodiments, memory 50 stores multiple sets of stimulation parameters that are available to be selected by patient 12 for delivery of neurostimulation therapy to the patient 12. For example, memory 50 may store stimulation parameters transmitted by clinician programmer 42.

Memory 50 also stores program instructions that, when executed by processor 48, cause neurostimulator 40 to deliver neurostimulation therapy. Memory 50 may include any volatile or non-volatile media, such as random access memory (RAM), random read-only memory (ROM), compact disc-read-only memory (CD-ROM), non-volatile random access memory (NVRAM), electrically erasable programmable read-only memory (EEPROM), flash memory, and the like. Accordingly, computer-readable media storing instructions may be provided to cause processor 48 to provide functionality as described herein.

In some embodiments a telemetry circuit 52 can support wireless communication between two or more of neurostimulator 40, clinician programmer 42, and patient programmer 43. In addition, in some embodiments, telemetry circuit 52 supports wireless communication with one or more wireless sensors that sense physiological signals and transmit the signals to neurostimulator 40 clinician programmer 42, patient programmer 43 or some combination thereof.

As mentioned above, migration of lead 10 can have detrimental effects on the efficacy of neurostimulation therapy for a patient 12. Fixing the neurostimulation lead 10 to surrounding tissue may prevent harmful effects that may result from a loose neurostimulation lead 10. As described below, a lead in accordance with the invention may provide fixation (not shown in FIGS. 1A through 1D) between the lead 10 and tissue surrounding the lead 10, such as tissue within the sacrum 16, without the need for surgical implantation techniques, such as sutures.

Leads in accordance with the invention can be utilized for electrical stimulation of body tissue and include at least one shape memory polymer portion that has a first configuration and a second configuration, wherein the second configuration is obtained after exposure to a transition stimulus, and wherein the second configuration of the shape memory polymer portion exhibits a greater resistance to movement of the lead within the body tissue than does the first configuration, and at least one electrode configured to provide electrical stimulation of body tissue.

Leads of the invention include at least one shape memory polymer portion. As used herein, a shape memory polymer portion is a portion of the lead that is capable of having at least two different configurations, a first configuration and a second configuration after being exposed to a transition stimulus.

The second configuration exhibits a greater resistance to movement of the lead within the body tissue than does the first configuration. For example, the first configuration could be straight and the second configuration could be a helix.

The shape memory polymer portion of a lead in accordance with the invention can be made at least in part of at least one material that is capable of being deformed and fixed into a temporary shape, and recover its original permanent shape upon exposure to a transition stimulus. Currently there are shape memory polymers that are known to be either thermo-responsive or photoresponsive.

In one embodiment of the invention any shape memory polymer or polymer can be used to produce the shape memory polymer portion of the lead. Examples of which include, but are not limited to, the materials and the manufacturing methods described in U.S. Pat. No. 6,160,084; U.S. Pat. No. 6,270,402; U.S. Pat. No. 6,338,043; US 2005/0036045; and CA 2527976, the disclosures of which are incorporated herein by reference.

Shape memory polymers with a thermally induced shape memory effect, that respond to a thermal transition stimulus, have at least one switching segment with a transitional temperature, otherwise known as a switching temperature. The switching segments form temporary cross linking portions, which resolve when heated above the transitional temperature and which form again when being cooled. The transitional temperature may be a glass temperature $T_g$ of amorphous ranges or a melting temperature $T_m$ of crystalline ranges. The transitional temperature is referred to herein as $T_{trans}$. At this temperature the shape memory polymer shows a change in shape.

Above $T_{trans}$ the shape memory polymer material is in the amorphous state and is elastic. If a sample is heated above $T_{trans}$, deformed in the flexible state, and then cooled down below $T_{trans}$, the chain segments are fixed by freezing degrees of freedom in the deformed state (programming). Temporary cross linking portions (non-covalent) are formed so that the sample cannot return to its original shape without an external load. When re-heating to a temperature above $T_{trans}$, these temporary cross linking portions are resolved and the sample returns to its original shape, by re-programming, the temporary shape can be produced again.

In one embodiment of the invention, the shape memory polymer portion of a lead in accordance with the invention can include thermoplastic elastomers, multiblock copolymers of macrodiols based on pentadeclaracton (PDL) and caprolacton (PCL) and a diisocyanate, polymer networks, amorphous polyurethane networks of trioles and/or tetroles and diisocyanate, and functionalized macrodiols corresponding to $\alpha,\omega$-divinyl compounds.

In another embodiment, photosensitive shape memory polymers can be utilized. Suitable photosensitive networks can be amorphous and can be characterized by covalent network points, which determine the second configuration of the shape memory polymer portion.

Shape memory polymers with a photosensitive induced shape memory effect, that respond to a particular wavelength of light as the transition stimulus, have photo-reactive groups, which can reversibly be linked with one another by irradiation with light. These photo-reactive groups take over the function of the switching segment in the shape memory polymers with thermal transitions. The programming of a temporary shape and re-generation of the permanent shape takes place in this case by irradiation without a change in temperature being necessary.

A network which includes photosensitive substituents along the amorphous chain segments. When being irradiated with UV light, these groups are capable of forming covalent bonds with one another. If the material is deformed and irradiated by light of a suitable wavelength, the original network is additionally cross-linked. Due to the cross-linking a temporary fixing of the material in deformed state is achieved (programming). Since the photo-linking is reversible, the cross linking can be released again by further irradiation with light of a different wavelength/2 and thus the original shape of the material can be reproduced again (reproduction). Such a photo-mechanical cycle can be repeated arbitrarily often. The basis of the photo-sensitive materials is a wide meshed polymer network, which, as mentioned above, is transparent in view of the irradiation intended to activate the change in shape. Networks utilized as shape memory polymers in the invention can be based on low-molecular acrylates and methacrylates, which can radically be polymerized. As a co-monomer for producing the polymer network of the present invention a component is used, which is responsible for the cross linking of the segments. The chemical nature of this component of course depends on the nature of the monomers.

Examples of suitable materials include, but are not limited to, networks based on acrylatemonomers are crosslinked with bi-functional acrylate compounds for example, which are suitably reactive with the starting materials for the chain segments so that they can be converted together. Cross linking agents of this type comprise short, bi-functional cross linking agents, such as ethylenediacrylate, low-molecular bi- or polyfunctional cross linking agents, oligomer, linear diacrylate cross linking agents, such as poly(oxyethylene)diacrylates or poly(oxypropylene)diacrylates and branched oligomers or polymers with acrylate end groups.

Polymer networks that can be a component of shape memory polymers for use in the invention also include a photoreactive component (group), which is responsible for the activation of the change in shape that can be controlled via the transition stimulus. This photo-reactive group is a unit which is capable of performing a reversible reaction caused by the stimulation of a suitable light irradiation, in one embodiment UV radiation (with a second photo-reactive group), which leads to the generation or resolving of covalent bonds. Exemplary photo-reactive groups include, but are not limited to groups that are capable of performing a reversible photodimerization. Different cinnamic acid esters (cinnamates, CA) and cinnamylacylic acid ester (cinnamylacylates, CM) can be used as photo reactive groups.

It is also known that cinnamic acid and its derivatives dimerize under UV-light of approx. 300 nm by forming cyclobutane. These dimers can be split again if irradiation is carried out with a smaller wavelength, for example a wavelength of about 240 nm. The absorption maximum can be shifted by substituents on the phenyl ring, however they always remain in the UV range. Further derivatives that can be photodimerized, are 1.3-diphenyl-2-propene-1-on (chalcon), cinnamylacylic acid, 4-methylcoumarine, various orthos-substituted cinnamic acids, cinammolyxysilane (silyether of the cinnamon alcohol).

To process the thermoplastic elastomers to form shape memory polymer portions of leads of the invention conventional polymer-technical methods as would be known to one of skill in the art, having read this specification, can be utilized. Examples of which include, but are not limited to injection molding, extrusion, and rapid prototyping. Additionally, manufacturing methods such as laser cutting can be used. In the case of thermoplastic elastomers, different designs can be realized by spinning in mono and multi-filament threads with subsequent interweaving to a cylindrical network with a mesh structure.

Figure 2A:
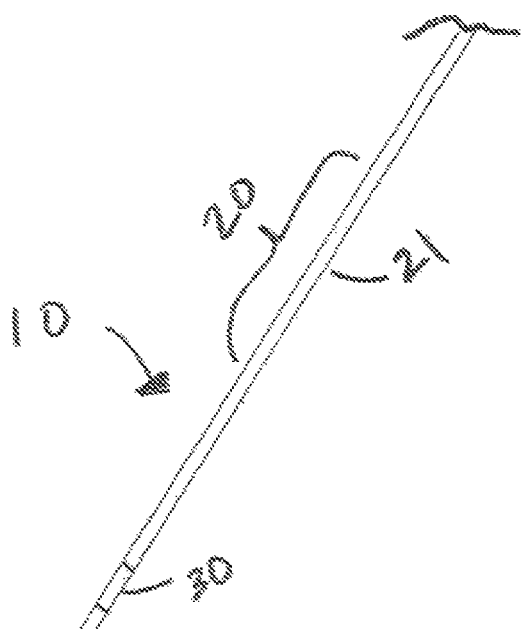
FIG. 2A is an exemplary embodiment of a portion of a lead in accordance with the invention before being exposed to a transition stimulus.
Figure 2B:
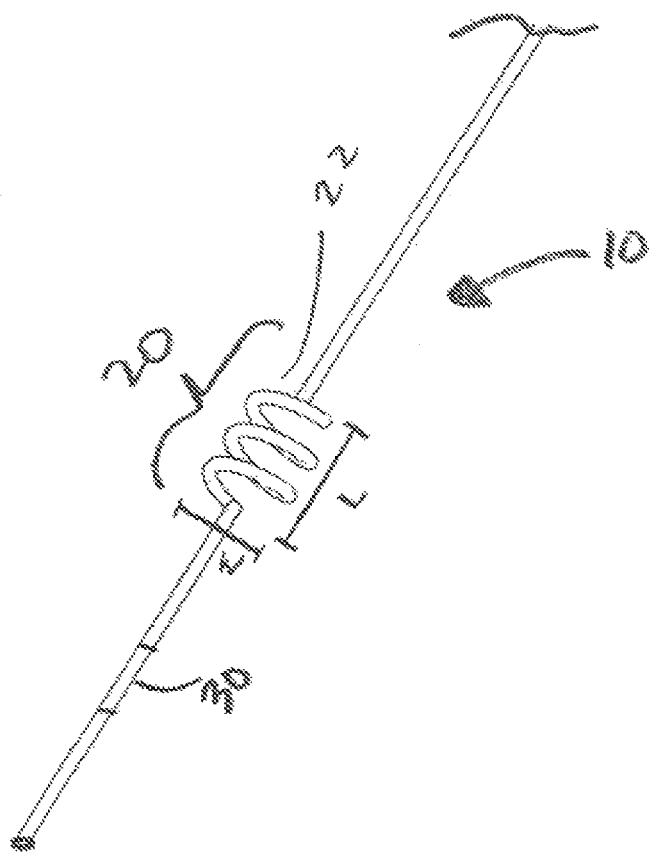
FIG. 2B is an exemplary embodiment of a portion of a lead in accordance with the invention after being exposed to a transition stimulus.

FIGS. 2A and 2B offer an example of a lead 10 before being exposed to a transition stimulus (FIG. 2A) and after being exposed to a transition stimulus (FIG. 2B). As seen there, the shape memory polymer portion 20 goes from a substantially straight configuration 21 to a spiral or helical configuration 22. In one embodiment a helical configuration may provide advantages because it may provide fixative capabilities and strain relief. The strain relief may be able to accommodate any sudden, large displacement of the lead by absorbing the forces in the "spring" like helical structure.

In an embodiment of a lead in accordance with the invention that includes a helical second configuration that is designed to be used for stimulation within the pelvic region, the helical configuration can generally have a length L (as shown in FIG. 2B) from about 5 mm to about 25 mm. In another embodiment, the length L of the helical configuration is from about 10 mm to about 20 mm. In yet another embodiment the length L of the helical second configuration is about 13 mm to about 17 mm. One of skill in the art will understand that different lengths L could be utilized depending on both the type of tissue that the lead is to be fixated in and the anatomy of the surrounding location of implantation.

In an embodiment of a lead in accordance with the invention that includes a helical second configuration that is designed to be used for stimulation within the pelvic region, the helical configuration can generally have a width W (as shown in FIG. 2B) from about 3 mm to about 20 mm. In another embodiment, the width W of the helical configuration is from about 6 mm to about 12 mm. In yet another embodiment the width W of the helical second configuration is about 8 mm to about 10 mm. Embodiments of the invention can also have a width W that varies over the length L of the second helical configuration.

Embodiments of the invention can also have a width W that varies over the length L of the second helical configuration. In one embodiment the width W can be greater at the distal end (distal end is the end of the second helical configuration that is closest to the distal tip of the lead) than it is at the proximal end of the second helical configuration, for example. In one embodiment of the invention, the most distal edge of the helical second configuration could have a smaller coil diameter. Such an embodiment may allow the coil of the second helical configuration to form gradually, which may be less likely to change the proximity of the electrodes to the nerve. One of skill in the art will understand that different widths W could be utilized depending on both the type of tissue that the lead is to be fixated in and the anatomy of the surrounding location of implantation.

In one embodiment of the invention that is designed to be used for implantation within the pelvic floor for sacral nerve stimulation, the lead may be configured so that the second configuration lies in close proximity to the foramen after the lead is implanted. In another embodiment of the invention that is designed to be used for implantation within the pelvic floor for sacral nerve stimulation, the lead may be configured so that the second configuration forms within the foramen. Such a lead could allow the second configuration to act against the bone and the inside of the foramen, or on either side of the facial layer covering the foramen to further anchor the lead where it is implanted.

Figure 3A:
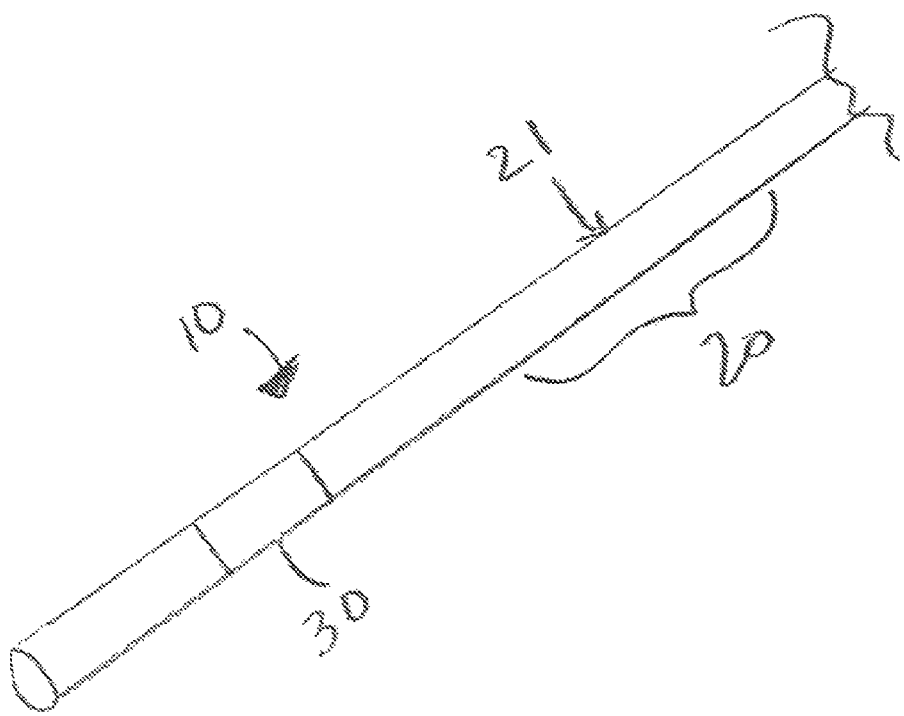
FIG. 3A is an exemplary embodiment of a portion of a lead in accordance with the invention before being exposed to a transition stimulus.
Figure 3B:
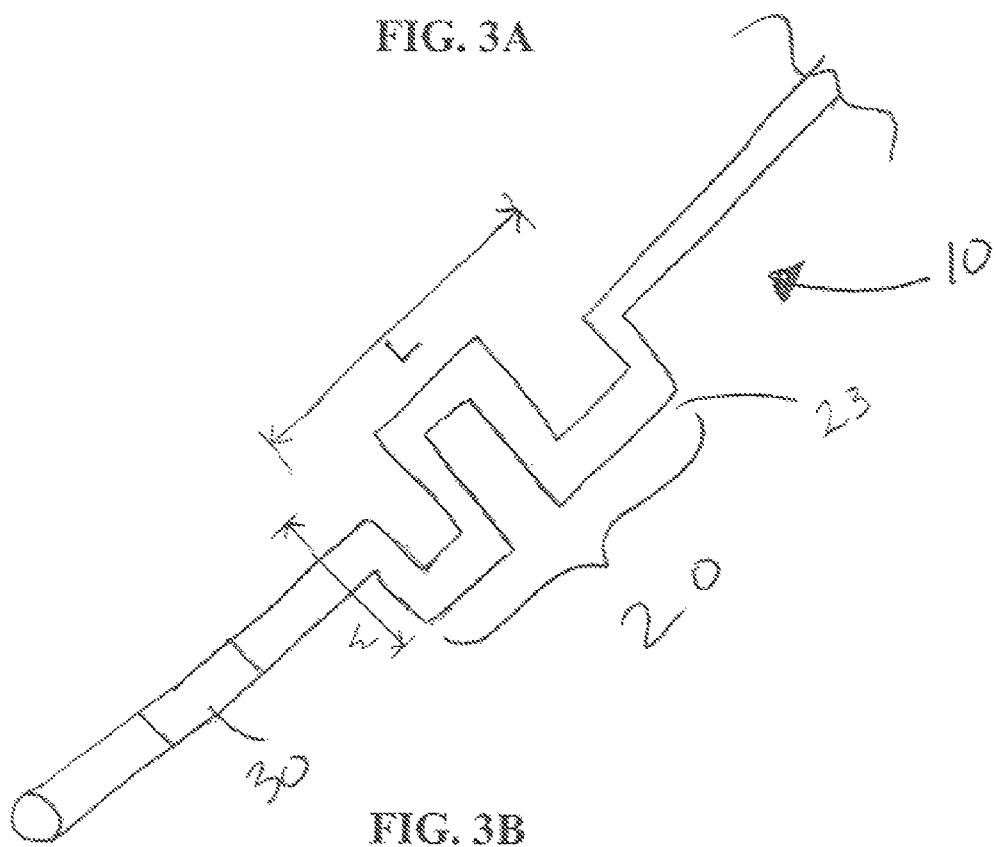
FIG. 3B is an exemplary embodiment of a portion of a lead in accordance with the invention after being exposed to a transition stimulus.

FIGS. 3A and 3B offer another example of a lead 10 while exposed to a first temperature (FIG. 3A) and while exposed to a second temperature (FIG. 3B). As seen there, the modifiable portion goes from a substantially straight configuration 21 to a stepped configuration 23 such as a square wave or a more rounded configuration having a more sigmoid shape (similar to a sine wave). In one embodiment a stepped configuration could form its shape at the facial layer that covers the foramen. In such an embodiment, the step in the lead could form a right angle distal to the puncture through the facia, which could provide excellent tensile resistance from pulls on the lead body that would normally dislodge the lead.

In an embodiment of a lead in accordance with the invention that includes a stepped second configuration that is designed to be used for stimulation within the pelvic region, the stepped configuration can generally have a length L (as shown in FIG. 3B) from about 5 mm to about 30 mm. In another embodiment, the length L of the stepped configuration is from about 10 mm to about 20 mm. In yet another embodiment the length L of the stepped second configuration is about 13 to about 17 mm. One of skill in the art will understand that different lengths L could be utilized depending on both the type of tissue that the lead is to be fixated in and the anatomy of the surrounding location of implantation.

In an embodiment of a lead in accordance with the invention that includes a stepped second configuration that is designed to be used for stimulation within the pelvic region, the stepped configuration can generally have a width W (as shown in FIG. 3B) from about 3 mm to about 20 mm. In another embodiment, the width W of the stepped configuration is from about 6 mm to about 12 mm. In yet another embodiment the width W of the stepped second configuration is about 8 mm to about 10 mm. Embodiments of the invention can also have a width W that varies over the length L of the second stepped configuration. In one embodiment the width W can be greater at the distal end (distal end is the end of the second stepped configuration that is closest to the distal tip of the lead) than it is at the proximal end of the second stepped configuration, for example. One of skill in the art will understand that different widths W could be utilized depending on both the type of tissue that the lead is to be fixated in and the anatomy of the surrounding location of implantation.

Figure 4A:
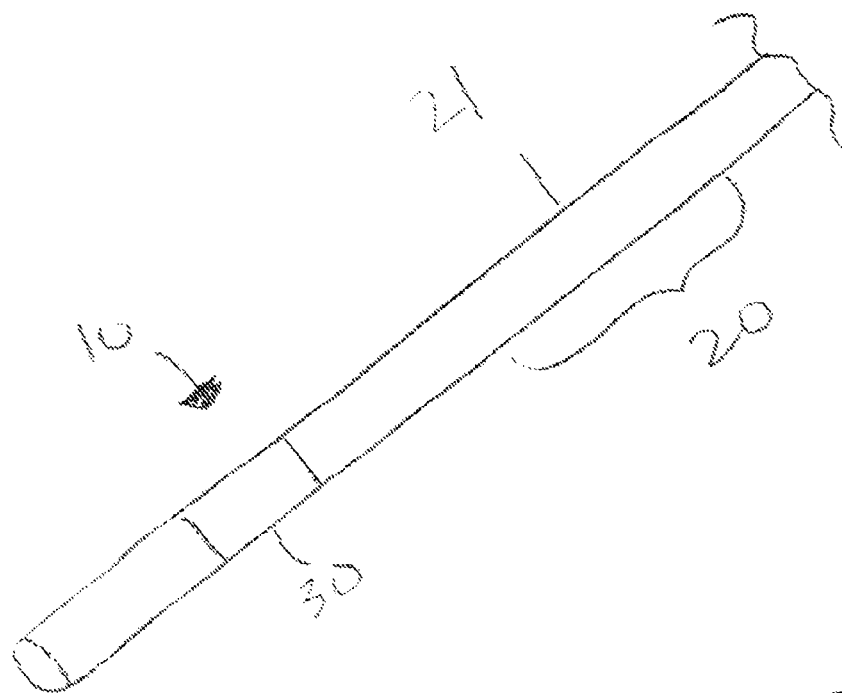
FIG. 4A is an exemplary embodiment of a portion of a lead in accordance with the invention before being exposed to a transition stimulus.
Figure 4B:
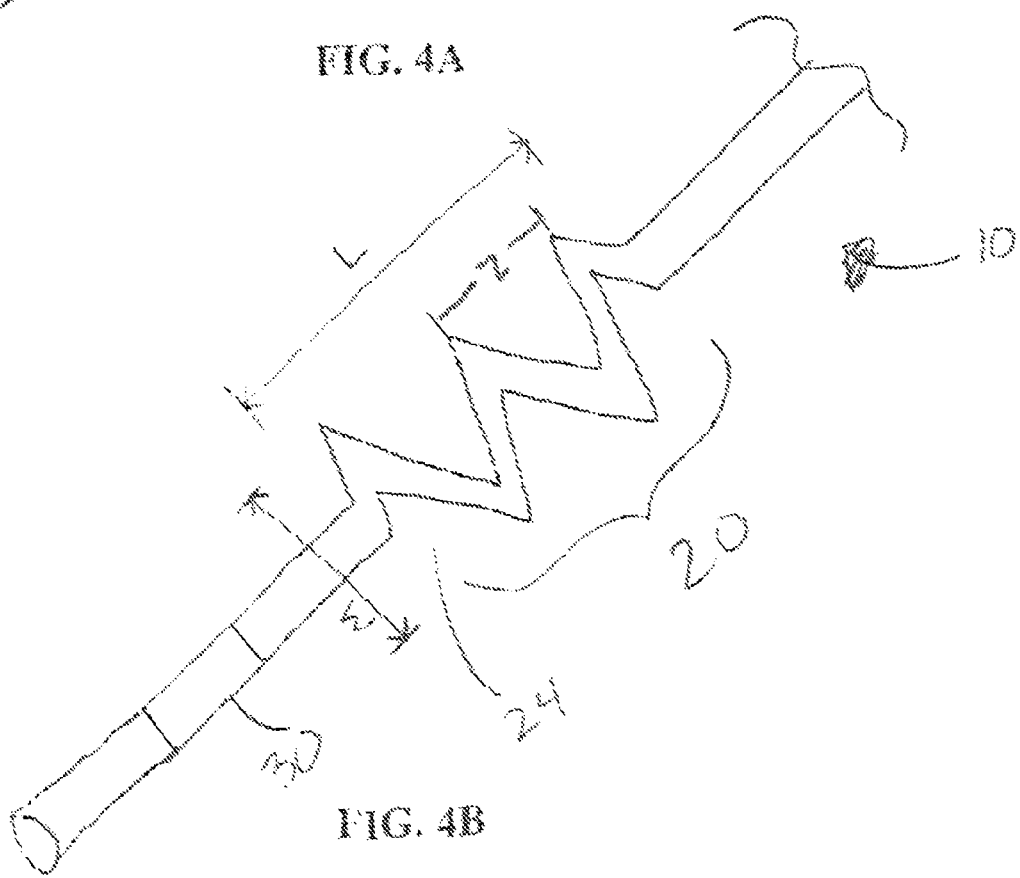
FIG. 4B is an exemplary embodiment of a portion of a lead in accordance with the invention after being exposed to a transition stimulus.

FIGS. 4A and 4B offer another example of a lead 10 while exposed to a first temperature (FIG. 4A) and while exposed to a second temperature (FIG. 4B). As seen there, the modifiable portion goes from a substantially straight configuration 21 to a zigzag configuration 24 (similar to a sawtooth waveform). In one embodiment a zigzag configuration could provide with a more pointed geometry at the width excursions could provide more burrowing ability into the surrounding tissue. That may allow more pressure to be exerted at the tip of the width features and thereby provide the desired strain relief and fixation.

In an embodiment of a lead in accordance with the invention that includes a zigzag second configuration that is designed to be used for stimulation within the pelvic region, the zigzag configuration can generally have a length L (as shown in FIG. 4B) from about 5 mm to about 30 mm. In another embodiment, the length L of the zigzag configuration is from about 10 mm to about 20 mm. In yet another embodiment the length L of the zigzag second configuration is about 13 mm to about 17 mm. One of skill in the art will understand that different lengths L could be utilized depending on both the type of tissue that the lead is to be fixated in and the anatomy of the surrounding location of implantation.

In an embodiment of a lead in accordance with the invention that includes a zigzag second configuration that is designed to be used for stimulation within the pelvic region, the zigzag configuration can generally have a width W (as shown in FIG. 4B) from about 3 mm to about 20 mm. In another embodiment, the width W of the zigzag configuration is from about 6 mm to about 12 mm. In yet another embodiment the width W of the zigzag second configuration is about 8 mm to about 10 mm. Embodiments of the invention can also have a width W that varies over the length L of the second zigzag configuration. In one embodiment the width W can be greater at the distal end (distal end is the end of the second zigzag configuration that is closest to the distal tip of the lead) than it is at the proximal end of the second zigzag configuration, for example. One of skill in the art will understand that different widths W could be utilized depending on both the type of tissue that the lead is to be fixated in and the anatomy of the surrounding location of implantation.

In one embodiment having a zigzag configuration, the point to point distance Z (on FIG. 4B) can also be modified based on factors such as the type of tissue that the lead is to be fixated in and the anatomy of the surrounding location of implantation. In one embodiment of the invention, the point to point distance Z can range from about 2 mm to about 6 mm.

One of skill in the art, having read this specification, will also understand that the at least one shape memory polymer portion 20 of a lead 10 in accordance with the invention could have other types of second configurations. The second configuration provides a greater resistance to movement of the lead 10 within the body tissue than does the first configuration. Geometric second configurations that cause a greater resistance to movement of the lead 10 within the body tissue that were not exemplified herein are also included in the scope of this invention.

FIG. 5 depicts another exemplary embodiment of a lead 10 in accordance with the invention. As seen in FIG. 5, a lead 10 in accordance with the invention has a spacer distance s between the shape memory polymer portion and the most proximal electrode. In leads having more than one shape memory polymer portion, the spacer distance s between the most proximal electrode and the first shape memory polymer portion and the spacer distance s between the first shape memory polymer portion and the second shape memory polymer portion need not, but can be the same. One of skill in the art, having read this specification, will understand that whether or not the spacer distances s are the same, can depend at least in part on considerations such as, the type of tissue that the lead is to be implanted in, the surrounding anatomy where the lead will be implanted, the particular configuration of the second configuration of the shape memory polymer portion, the number of shape memory polymer portions within the lead, and the location of the at least one shape memory polymer portion within the lead.

In one embodiment, spacer distance s can range from about 1 mm to about 20 mm. In another embodiment, spacer distance s can range from about 5 to about 15 mm. In yet another embodiment, spacer distance s is about 10 mm. One of skill in the art, having read this specification, will understand that any particular spacer distance s can vary depending at least in part on considerations such as, the type of tissue that the lead is to be implanted in, the surrounding anatomy where the lead will be implanted, the particular configuration of the second configuration of the shape memory polymer portion, the number of shape memory polymer portions within the lead if there is more than one, and the location of the one or more shape memory polymer portions within the lead.

As described above, a lead 10 may include at least one shape memory polymer portion 20 to fix the lead in any tissue surrounding the lead, such as tissue within an epidural region or tissue within or near a foramen 14 of sacrum 16 for example. At least one shape memory polymer portion 20 may be located between electrodes 30 at a distal end of lead 10, or at a proximal end of lead 10. In one embodiment, at least one shape memory polymer portion 20 may be disposed proximal to the electrode 30 near the distal end 31 of lead 10 in order to fix the electrodes in place relative to a target stimulation site.

In one embodiment, a lead in accordance with the invention may have more than one shape memory polymer portion 20. In one embodiment of the invention, a lead of the invention may have 1, 2, 3, 4, or more shape memory polymer portions.

As discussed above, a lead in accordance with the invention has at least one shape memory polymer portion that has a first configuration before being exposed to a transition stimulus and a second configuration after being exposed to a transition stimulus. Transition stimuli can include adding energy to heat the shape memory polymer to a particular temperature, the transition temperature, or adding energy of a particular wavelength. In embodiments of the invention that use a thermoresponsive shape memory polymer, the transition stimulus, adding energy to heat the shape memory polymer to the transition temperature, can be accomplished by embedding a heating element with the shape memory polymer portion, by flushing the shape memory polymer portion with a heated liquid, such as saline, by applying infrared (IR) or near infrared (NIR) radiation, by applying an oscillating electrical field, or other methods of heating the shape memory polymer to a temperature at or above the transition temperature. In embodiments of the invention that use a photoresponsive shape memory polymer, the transition stimulus can be applied by externally irradiating the shape memory polymer portion with the transition wavelength, or by internally irradiating the shape memory polymer with the transition wavelength.

When manufacturing a lead in accordance with this invention, the lead body, including the one or more electrode(s), the one or more shape memory polymer portion(s), and any other features of the lead can be manufactured as was known to one of skill in the art, having read this specification, at the time of the invention.

FIGS. 6-9 depict the primary steps of implanting the sacral nerve stimulation lead 10 of the invention. An introducer 200 receives the distal portion 31 of the lead including the at least one electrode 30 and the at least one shape memory polymer portion disposed within the lumen of the introducer 200. A stylet 100 can be disposed within the lead body lumen so that its distal tip closes the lumen distal end opening. The assembly can be advanced percutaneously at a selected angle until the introducer distal end is disposed at the selected foramen as shown in FIG. 6.

To determine the best location of the one or more electrodes, an insulated needle with both ends exposed for electrical stimulation can be used to locate the foramen and locate the sacral nerve by applying electrical stimulation through the needle using an external pulse generator. The efficacy of the location is tested by evaluating the physiologic response in relation to the electrical threshold energy required to elicit the response. For control of urinary incontinence, the physician can implant the medical electrical lead 10 near the S3 sacral nerves. The implantable medical electrical lead 10 may, however, be inserted near any of the sacral nerves including the S1, S2, S3, or S4, sacral nerves accessed via the corresponding foramen depending on the necessary or desired physiologic response.

The advancement of the introducer 200 can be accomplished separately over a guide wire previously percutaneously advanced from the skin incision into the foramen to establish the angle of advancement. Also, a two-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately provides the introducer 200 in the location depicted in FIG. 6.

The lead 10, optionally stiffened by the stiffening stylet 100 disposed in the lead lumen, is advanced through the introducer lumen proximal end opening into the introducer lumen. However it is accomplished, the at least one electrode 30 and the at least one shape memory polymer portion 20 are disposed within the introducer lumen pre-positioned to be implanted in relation to the sacral nerve accessed through the foramen and in the subcutaneous tissue, respectively.

Figure 7:
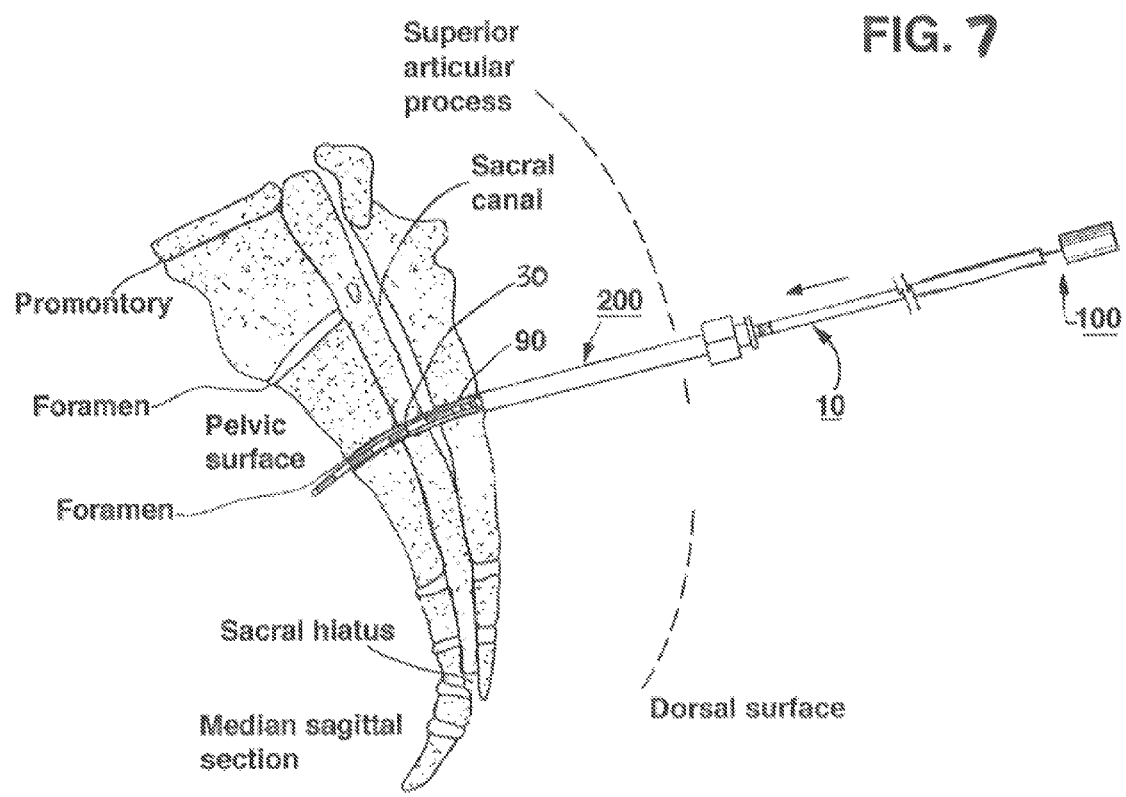
FIG. 7 is a cross-section view of the sacrum schematically illustrating a further step of implanting a lead of the invention extending the one or more electrodes through a foramen.

The stylet 100 may be advanced distally through the foramen as depicted in FIG. 6 or the lead 10 and the stylet wire 100 can both be advanced distally out of the introducer lumen distal end opening to advance the at least one electrode 30 into or through the foramen from the posterior entrance into casual contact with the more anterior sacral nerve as shown in FIG. 7.

After electrical testing to establish optimal positioning is completed the introducer 200 is retracted proximally. The at least one shape memory polymer portion 20 is now exposed to the transition stimulus. Exposing the shape memory polymer portion 20 to the transition stimulus can be accomplished as would be known to one of skill in the art, having read this specification. In embodiments of the invention where the shape memory polymer portion is a thermoresponsive polymer, the transition stimulus can be applied via an embedded heating element in the shape memory polymer, via flushing the shape memory polymer portion with warmed fluid, via application of IR or NIR radiation, or via an oscillating electrical field. In embodiments where the shape memory polymer material is a photoresponsive polymer, the transition stimulus can be applied via application of the correct wavelength of light.

After the lead has been properly placed, for example, with one of the electrodes in close proximity to the target peripheral nerve, the stylet of the lead may be removed. A fiber optic can then be used in the lumen space to transmit light of the correct wavelength or energy to heat the polymer to the shape memory polymer portion 20 of the lead. Alternatively, the proximal portion of the lead may be placed in a receptacle and the light energy may be coupled directly into the lead's insulation and brought to the shape memory polymer portion 20 of the lead.

In embodiments of the invention where the shape memory polymer portion of the lead is made of a photoresponsive polymer, the shape memory polymer portion 20 can be manipulated into the second configuration when the polymer material is illuminated, for example, with ultraviolet light with a wavelength longer than 260 nanometers (nm). The lead body may even be returned back to the original shape when illuminated with ultraviolet light with a wavelength shorter than 260 nm. Such an embodiment may be useful for removing the lead after the shape memory polymer portion of the lead has regained its first configuration. An embodiment that can shift between the two configurations with wavelengths longer and shorter than 260 nm can be accomplished using a mix of polymers in the shape memory polymer portion of the lead. The first polymer in such an embodiment would form the first configuration and the second polymer would be capable of forming cross links in the presence of ultraviolet light longer than 260 nm. Exposing the material to the shorter wavelength would break the cross-links, which would allow the material to recover its original shape.

Figure 8:
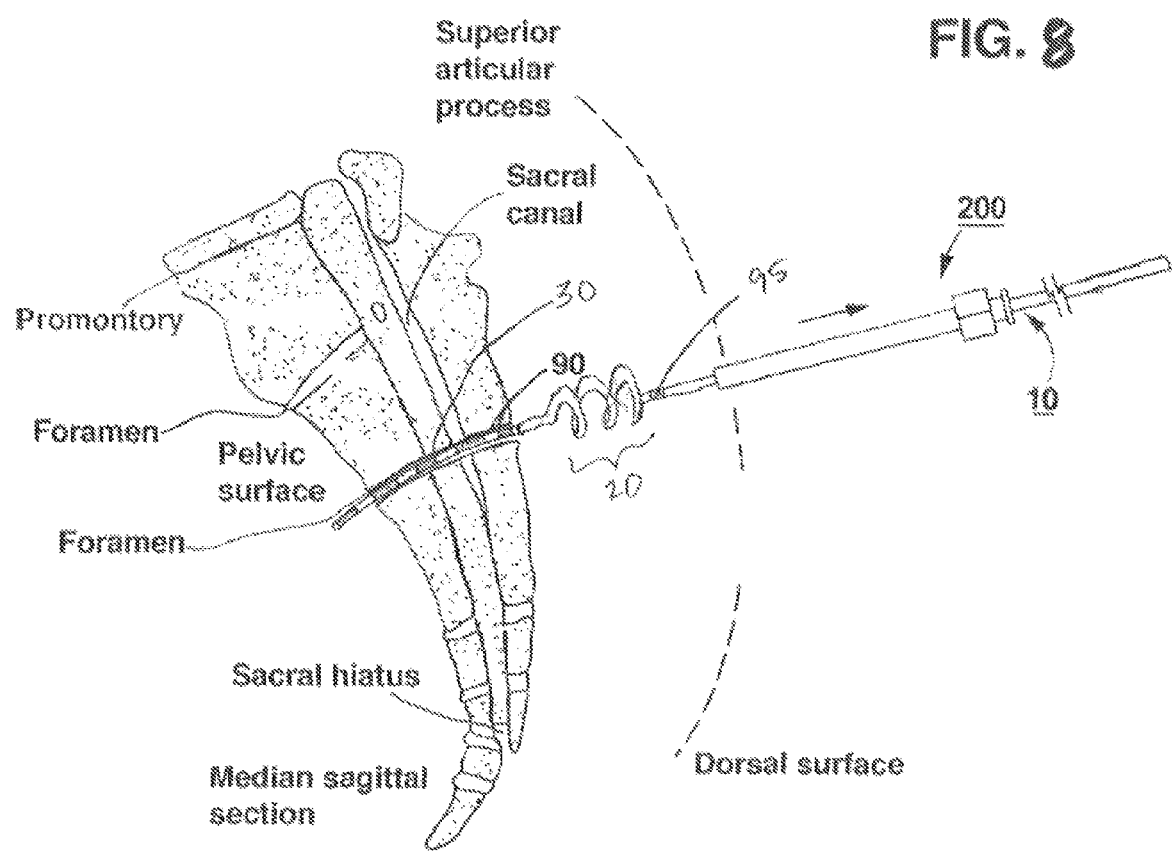
FIG. 8 is a cross-section view of the sacrum schematically illustrating a further step of implanting a lead of the invention retracting the introducer and after the shape memory polymer portion was exposed to a transition stimulus.
Figure 9:
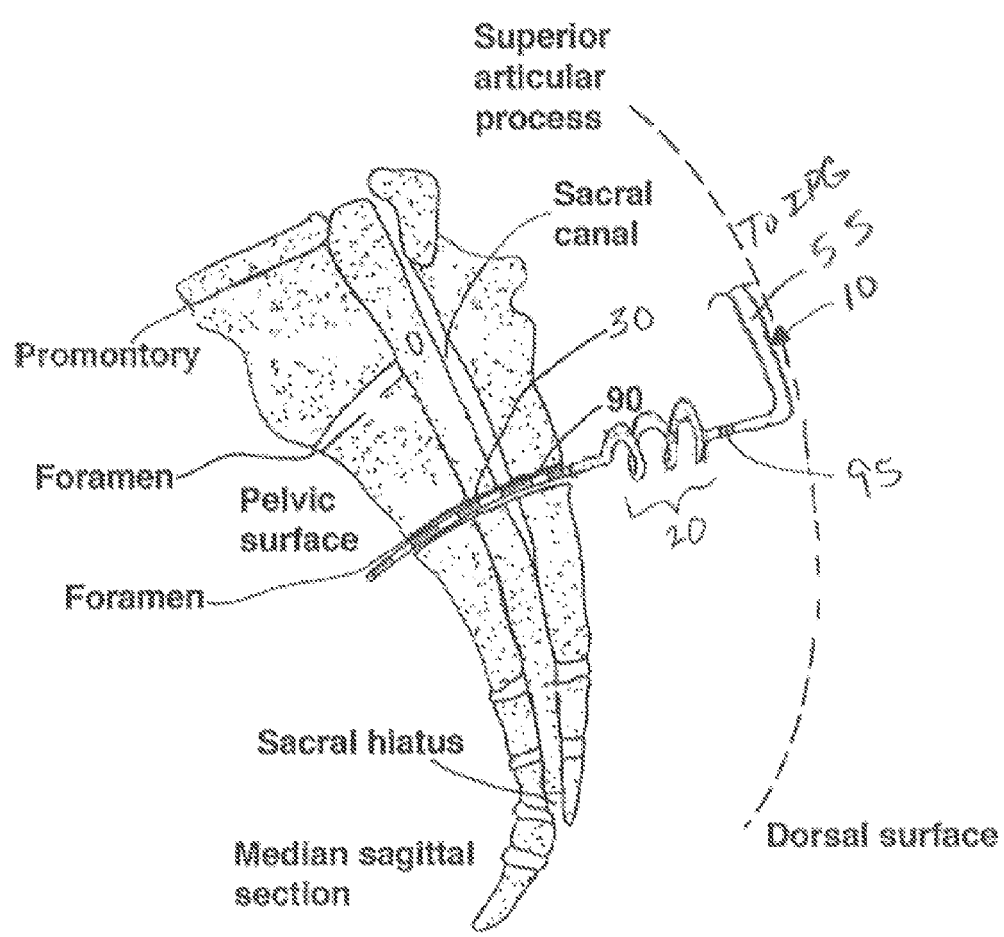
FIG. 9 is a cross-section view of the sacrum schematically illustrating a further step of implanting a lead of the invention subcutaneously routing the proximal portion of the lead body to the implantation site of the neurostimulator IPG.

The introducer 200 and lead stylet 100, if present, are completely removed in FIG. 8. As shown in FIG. 9, the proximal portion 55 of the lead 10 is bent laterally with respect to the distal portion of the lead 10 and implanted through a subcutaneously tunneled path to the neurostimulator IPG.

In one embodiment of the invention, a lead 10 can include one or more markers, of which marker 90 is an example. Such markers can be made of materials that can be visualized under fluoroscopy. This can allow the physician to more easily see where the particular parts of the lead 10 are within the patient. For example, a lead that has a first marker 90 on the distal end of a shape memory polymer portion 20 and a second marker 95 (as seen in FIGS. 8 and 9) on the proximal end of the shape memory polymer portion, can allow the position of the shape memory polymer portion 20 to be easily located within the patient. When the shape memory polymer portion 20 transitions into the second configuration, it bears against the tissue and inhibits proximal retraction of the lead body through the subcutaneous tissue if traction is applied to the lead body since the second configuration resists inversion, migration, retraction, and displacement in the proximal direction. Leads in accordance with the invention can also provide strain relief between proximal forces (or strains) in the lead body and the desired location of the electrodes.

The medical electrical leads and procedures of the present invention can be used to stimulate multiple nerves or multiple sides of a single nerve bundle. It should also be understood that although sacral nerve stimulation was exemplified herein, the leads of the invention can be used for other types of nerve stimulation. In addition, the medical electrical lead 10 can also be used as an intramuscular lead where the at least one shape memory polymer portion can engage against muscle and assist in preventing dislodgement of the at least one electrode. This may be useful in muscle stimulation such as dynamic gracioplasty or stomach stimulation for gastroparesis or obesity.

Although the invention has been described in detail with particular reference to a certain embodiments thereof, it will be understood variations and modifications can be effected within the scope of the following claims. Such modifications may include substituting elements or components which perform substantially the same function in substantially the same way to achieve substantially the same result for those described herein.

We claim:

1. An implantable medical electrical lead for electrical stimulation of body tissue comprising:
    a lead body;
    at least one shape memory polymer portion that forms a section of the lead body such that the shape memory polymer portion is between two linear portions of the lead body, the shape memory polymer portion having a first configuration where the shape memory polymer portion has a coaxial relationship with the two portions of the lead body and has a second configuration, wherein the second configuration is obtained upon exposure of the shape memory polymer portion to a transition stimulus, wherein the second configuration of the modifiable portion exhibits a greater resistance to movement of the lead within the body tissue than does the first configuration and wherein the second configuration is a helical configuration with a coil diameter of the helical configuration being smaller at a distal edge of the shape memory polymer portion than at a proximal end of the shape memory polymer portion and with a longitudinal axis of a helix formed by the helical configuration being co-linear with a longitudinal axis of the lead body; and at least one electrode configured to provide electrical stimulation of body tissue, wherein the lead body has a proximal end and a distal end.

2. The implantable lead according to claim 1, wherein the shape memory polymer portion is made of one or more photoresponsive polymers.

3. The implantable lead according to claim 1, wherein the shape memory polymer portion is made of one or more thermoresponsive polymers.

4. The lead according to claim 1, wherein the at least one shape memory polymer portion is from about 5 mm to about 30 mm.

5. The lead according to claim 1, wherein the at least one shape memory polymer portion is from about 13 mm to about 17 mm.

6. The lead according to claim 1, wherein the lead has two or more electrodes.

7. The lead according to claim 1, wherein the lead has at least four electrodes.

8. The lead according to claim 1, wherein there are two or more modifiable portions.

9. The lead according to claim 1, wherein the transition stimulus is heat.

10. The lead according to claim 1, wherein the transition stimulus is a particular wavelength of light.

11. A kit comprising:
an implantable medical electrical lead for electrical stimulation of body tissue comprising:
at least one electrode;
a lead body having a lumen;
at least one photoresponsive shape memory polymer portion that forms a section of the lead body and that has a first configuration where the shape memory polymer portion has a coaxial relationship with the lead body has and a second configuration, and wherein the second configuration is obtained upon exposure of the shape memory polymer portion to a transition stimulus, wherein the first configuration of the modifiable portion allows for movement of the lead body relative to the body tissue and the second configuration of the modifiable portion anchors the lead within the body tissue; and
a source of the transition stimulus that has a receptacle where a proximal portion of the lead body is positioned such that the transition stimulus is directly coupled into the lead body that couples the transition stimulus from the source to the shape memory polymer portion where the shape memory polymer portion is located distally of the proximal portion of the lead body.

12. The kit according to claim 11, wherein the at least one modifiable portion is from about 5 mm to about 30 mm.

13. The kit according to claim 11, wherein the at least one modifiable portion is from about 13 mm to about 17 mm.

14. The kit according to claim 11, wherein the lead has two or more electrodes.

15. The kit according to claim 11, wherein the lead has at least four electrodes.

16. The kit according to claim 11, wherein there are two or more shape memory polymer portions.

17. The kit according to claim 11, wherein the source of a transition stimulus is a source of UV radiation.

18. A medical electrical stimulation system comprising:
an implantable pulse generator for providing medical electrical stimulation; and
an implantable medical electrical lead for electrical stimulation of body tissue comprising:
a lead body having a lumen;
at least one thermoresponsive shape memory polymer portion that forms a section of the lead body and that has a first configuration where the shape memory polymer portion is substantially straight and has a coaxial relationship with the substantially straight portions of the lead body on each side of the shape memory polymer portion and has a second configuration, wherein the second configuration is obtained upon exposure of the shape memory polymer portion to a heat transition stimulus, and wherein the second configuration of the modifiable portion is a helix whose diameter changes over the length of the helix and the diameter of the helix being smaller at a distal edge of the shape memory polymer portion that at a proximal end of the shape memory polymer portion, and exhibits a greater resistance to movement of the lead within the body tissue than does the first configuration with the substantially straight portions of the lead body on each side of the helix;
a heating element embedded into the at least one helical shape memory polymer portion that provides the heat transition stimulus; and
at least one electrode configured to provide electrical stimulation of body tissue.

19. The system according to claim 18, wherein the lead has two or more electrodes.

20. The system according to claim 18, wherein the lead has at least four electrodes.

21. The system according to claim 18, wherein there are two or more shape memory polymer portions.

22. An implantable medical electrical lead for electrical stimulation of body tissue comprising:
at least one shape memory polymer portion that has a first configuration that is a substantially straight configuration provided by a first polymer of the at least one shape memory polymer portion and a second configuration that is provided by a second polymer of the at least one shape memory polymer portion, wherein the second configuration is obtained upon exposure of the second polymer of the shape memory polymer portion to a first transition stimulus and the first configuration is obtained upon exposure of the second polymer of the shape memory polymer portion to a second transition stimulus to allow the first polymer to produce the first configuration, wherein the second configuration of the modifiable portion exhibits a greater resistance to movement of the lead within the body tissue than does the first configuration; and
at least one electrode configured to provide electrical stimulation of body tissue, the electrode being positioned at a location along the lead that is distant from the at least one shape memory polymer portion,
wherein the lead has a proximal end and a distal end.

23. The implantable medical electrical lead of claim 22, wherein the at least one shape memory polymer portion provides strain relief relative to the location along the lead where the at least one electrode is located.

* * * * *

UNITED STATES PATENT AND TRADEMARK OFFICE
CERTIFICATE OF CORRECTION

| | | |
|---|---|---|
| PATENT NO. | : 8,135,476 B2 | |
| APPLICATION NO. | : 11/380499 | |
| DATED | : March 13, 2012 | |
| INVENTOR(S) | : Martin T. Gerber | |

It is certified that error appears in the above-identified patent and that said Letters Patent is hereby corrected as shown below:

In the Claims

<u>Claim 11, Column 17, line 34-35:</u> "lead body has and a second configuration" should read -- lead body and a second configuration --.

<u>Claim 18, Column 18, line 17-18:</u> "polymer portion that at a proximal end" should read -- polymer portion than at a proximal end --.

Signed and Sealed this
Seventeenth Day of March, 2015

Michelle K. Lee
*Director of the United States Patent and Trademark Office*